(12) United States Patent
Holzner et al.

(10) Patent No.: US 7,965,860 B2
(45) Date of Patent: Jun. 21, 2011

(54) DEVICE FOR SCANNING A TOOTH MODEL

(75) Inventors: Stephan Holzner, Hohenschäftlarn (DE); Gerhard Weber, Pürgen (DE)

(73) Assignee: Institut Straumann AG, Basel (CH)

( * ) Notice: Subject to any disclaimer, the term of this patent is extended or adjusted under 35 U.S.C. 154(b) by 1106 days.

(21) Appl. No.: 11/675,298

(22) Filed: Feb. 15, 2007

(65) Prior Publication Data

US 2007/0248929 A1    Oct. 25, 2007

(30) Foreign Application Priority Data

Feb. 16, 2006  (EP) ..................................... 06003191
Jan. 10, 2007  (EP) ..................................... 07000466
Jan. 22, 2007  (EP) ..................................... 07001336

(51) Int. Cl.
*G06K 9/00*        (2006.01)
(52) U.S. Cl. ......................... 382/100; 433/213; 433/223
(58) Field of Classification Search .................. 382/100, 382/128, 154; 433/24, 201.1, 213, 214, 223
See application file for complete search history.

(56) References Cited

U.S. PATENT DOCUMENTS

| | | | |
|---|---|---|---|
| 5,882,192 A | 3/1999 | Bergersen | |
| 6,287,121 B1 | 9/2001 | Guiot et al. | |
| 7,010,150 B1 * | 3/2006 | Pfeiffer et al. ................. | 382/128 |
| 7,020,325 B2 * | 3/2006 | Park ................................. | 382/154 |
| 7,106,958 B2 | 9/2006 | Kerschbaumer et al. | |
| 7,399,181 B2 | 7/2008 | Weber et al. | |
| 7,623,693 B2 * | 11/2009 | Holzner et al. ............... | 382/128 |
| 7,687,754 B2 * | 3/2010 | Eiff et al. .................... | 250/208.1 |
| 2002/0110786 A1 | 8/2002 | Dillier | |
| 2004/0032594 A1 | 2/2004 | Weber et al. | |
| 2004/0136580 A1 * | 7/2004 | Matsumiya et al. .......... | 382/128 |
| 2005/0060868 A1 | 3/2005 | McMurtry | |
| 2005/0095551 A1 | 5/2005 | Taub et al. | |
| 2005/0135874 A1 | 6/2005 | Baylis et al. | |
| 2006/0227338 A1 | 10/2006 | Buchler et al. | |

(Continued)

FOREIGN PATENT DOCUMENTS

DE           3640616 A1       6/1988

(Continued)

*Primary Examiner* — John B Strege
(74) *Attorney, Agent, or Firm* — IP Strategies (57) ABSTRACT

The present invention relates to a device for scanning a split-cast model, said split-cast model covering the area of a plurality of tooth sites and comprising a plurality of model parts, said device comprising: an optical scanning system (2) for one or for a plurality of split-cast models having a scanning area (3) with a width between 5 mm and 100 mm, the scanning system being adapted to be used for acquiring first data from a survey scan covering a plurality of model parts and second data from an individual scan covering only one model part, said first and second data representing the model with different/identical resolutions and/or different/identical completeness, a memory means for storing at least said first and second data, means for 3D matching said first and second data, a base plate, and further comprising a holding device for a split-cast model and/or individual model parts, which is adapted to be arranged on said base plate. In addition, the present invention relates to a device for scanning a split-cast model comprising a plurality of model parts, said device comprising a scanning system (2) for scanning the split-cast model, including a scanning area and a holding device (33) which is capable of holding a split-cast model as well as a model part. Furthermore, the present invention relates to a scanning device with a loading unit.

6 Claims, 7 Drawing Sheets

U.S. PATENT DOCUMENTS

| | | |
|---|---|---|
| 2006/0253212 A1 | 11/2006 | Weber et al. |
| 2007/0046663 A1 | 3/2007 | Brinkmann et al. |

FOREIGN PATENT DOCUMENTS

| | | |
|---|---|---|
| DE | 10352394 A1 | 11/2005 |
| DE | 102005016233 | 10/2006 |
| EP | 0913130 | 5/1999 |
| EP | 0913130 A2 | 5/1999 |
| EP | 1710536 A1 | 10/2006 |
| EP | 1757902 A1 | 2/2007 |
| WO | 0239056 A | 5/2002 |
| WO | WO-0239056 | 5/2002 |

* cited by examiner

DEVICE FOR SCANNING A TOOTH MODEL

FIELD OF THE INVENTION

The present invention relates to a device for scanning a tooth model.

BACKGROUND OF THE INVENTION

Devices for scanning tooth models so as to obtain a data set which digitally represents the tooth model are known. Such data sets can be used for the automatic production of dental prosthesis elements.

If different data sets each only represent part of a model and if the two data sets have, however, an area in which they overlap and represent the same part of the model, the two data sets can be combined by a matching process. The data in the overlapping area are used for defining or ascertaining the relative arrangement of the individual data sets. The data sets normally represent the shape of a surface in three dimensions. Hence, said matching is referred to as 3D matching. This matching can also be used for combining a larger number of data sets, e.g. 5, 10, 15 or 20 data sets, so as to obtain a single data set.

Tooth models can be provided in the form of so-called split-cast models. These models comprise a model part holder and removable model parts. The individual model parts correspond to individual portions of a model of a set of teeth, e.g. to one or a plurality of teeth or tooth sites. When the model parts are held by the model part holder, they represent a set of teeth or parts thereof. The model part holder defines the position of the individual model parts relative to one another.

A normal set of teeth of an adult comprises 32 tooth sites, 16 in the upper jaw and 16 in the lower jaw. Each tooth site is normally occupied by a tooth. A tooth site may, however, also be occupied by a dental prosthesis element or by parts of such an element or by implants or parts of such implants, such as implant abutments, or a residual tooth area or a gingival area. A tooth gap normally results in a gingival area at the tooth site. A tooth may also comprise dental prosthesis elements, such as fillings, inlays, overlays or the like. A residual tooth area can be a damaged tooth or a tooth prepared by the dentist (ground). A plurality of tooth sites can also be occupied by a dental prosthesis element, e.g. a bridge.

BRIEF SUMMARY OF THE INVENTION

It is the object of the present invention to improve known devices for scanning tooth models.

In the case of the device, an optical scanning system is provided, by means of which a model can be scanned in a scanning area. The width of the scanning area can be between 5 mm and 100 mm. In this interval a good resolution of the data will be achieved in combination with a sufficiently large scanning area of the model. The lower limit can also be 10, 15, 20, 25, 30, 35, 40, 45, 50, 55, 60, 65, 70, 75 mm. The upper limit can also be 10, 15, 20, 25, 30, 35, 40, 45, 50, 55, 60, 65, 70, 75, 80, 85, 90, 95 mm.

By means of the scanning system a scan can be made, which covers a plurality of model parts. The position of the model parts relative to one another can be determined in this way. Such as scan can also be referred to as survey scan. The model parts are inserted in the model part holder of the split-cast model.

Furthermore, it is possible to make a second scan (individual scan) or a plurality of such individual scans, which scan an individual model part. This scan is preferably made on a model part that has been removed from the model part holder of the split-cast model. The model part is here held independently of the model part holder of the split-cast model. The model part may, however, also be inserted in the model part holder. The adjoining model parts should, however, be removed so as to improve the optical accessibility to the model part.

The data of the first scan and of the second scan can have different resolutions. The data of the survey scan can e.g. be slightly coarser than those of the individual scan. They may, however, also have the same resolution or a higher resolution.

The data of an individual scan will normally represent the shape of a model part more completely than those of the survey scan, since no shading will be caused by neighbouring model parts. The individual scan is insofar more complete than the survey scan.

The first and second data can be stored and processed by a 3D matching means so as to obtain a single data set from the split-cast model or from a portion of said model.

The device includes a base plate. The base plate is preferably substantially flat on the upper surface thereof. It may, however, also have recesses, such as flutes, groove, holes or the like, and/or raised portions, such as pins, in said flat surface. Making use of these recesses and/or raised portions, other elements, such as an adapter and/or a holder, can be coupled to the base plate.

Furthermore, the device comprises a holding device that can be used for holding a split-cast model, a model part or a plurality of model parts or combinations thereof. The base plate, together with the holding device, allow the objects to be scanned to be arranged with great flexibility relative to the scanning area.

The base plate and the holding device are preferably implemented such that the holding device can be arranged on the base plate at an arbitrary position. The base plate may also comprise one or a plurality of snap-in locking devices for locking engagement with a holder. The base plate can also be provided with elements arranged in a raster, which allow an arrangement of the holding device at various defined raster positions. The elements (holes, pins, etc.) are preferably arranged periodically.

The base plate is preferably adapted to be rotated relative to the scanning area. Hence, various areas of the model can be scanned or made accessible for scanning. The base plate can have the form of a rotary disk. It can thus easily be fitted into a circular opening of the surrounding plate.

The base plate is preferably adapted to be linearly displaced. Various areas can thus be made accessible for scanning. The linear displaceability is preferably given in one or two directions (preferably perpendicular to one another).

The base plate is preferably vertically adjustable. On the one hand, the object to scanned can thus be positioned at a suitable distance from the optical scanning system. This can be relevant as far as the focussing of the illumination optics or of a recording optics is concerned. On the other hand, also the relation between the centre of rotation of the base plate and the scanning area on the base plate is changed by the respective height of the base plate (see below).

The possibility of holding the holding device on the base plate by means of a magnetic force is preferred. The force will normally be sufficiently strong for preventing an inadvertent displacement of the holding device, e.g. during a scan. Such fixing of the holding device can also easily be released without using any tools. Furthermore, it will allow an arrangement of the holding device on the base plate at any location and with any orientation.

The holding device is able to hold the object to be scanned at different heights above the base plate. For this purpose, it is possible to provide different holding devices on different levels or to provide vertically adjustable holding devices. It is thus possible to change the distance between the object to be scanned and the scanning system as well as the relation between the base plate and the scanning system (see below).

DE 103 04 111 A1 discloses a phase shift scanning method which can be used here. This document and the scanning method described therein as well as a correspondingly implemented device are referred to in their entirety, and the disclosure of this document is incorporated in the present application. In addition, laser line scanning methods are known, in the case of which a laser line is directed onto an object and records the object at a triangulation angle; the height profile can be concluded from the laser line image.

The scanning area of phase shift scanning can be square or rectangular (seen from above on the base plate). The edge length of the square or the edge length of each of the sides of the rectangle can be 5, 10, 15, 20, 25, 30, 35, 40, 45, 50, 55, 60, 65, 70, 75, 80, 85, 90, 95, 100, 110, 120 or 130 mm or it can lie in an interval defined by these values. All the possible interval combinations of the above-mentioned values are feasible.

According to an advantageous embodiment, the device is provided with a displacement means with the aid of which an axis of rotation can be displaced relative to the scanning area. An axis of rotation can thus be created outside of the scanning area as well as inside the scanning area. The first case allows the centre of a dental arch to be arranged on or close to the axis of rotation, whereas the dental arch itself is located in the scanning area. In the second case, a model part centre can be arranged on or close to the axis of rotation, said model part centre being located in the scanning area.

For displacing the rotary shaft, one or a plurality of linear displacement tables or an adapter can be provided. The rotary shaft can also be tilted additionally or alternatively, since this will allow a scanning system to see a tooth model to be scanned from a different angle. The adapter is provided with a rotary element which is mechanically coupled to the base plate by the adapter so that the rotary element will rotate when the base plate rotates. The rotary element can have an axis of rotation that is displaced in comparison with the axis of rotation of the base plate.

If the scanning area defines a plane in which said scanning area lies, it will in particular be advantageous to displace the axis of rotation along or parallel to said plane. Independently of a possible displacement component, this displacement can also take place in a direction transversely to said plane.

An adjustment aid will be of advantage as well. This adjustment aid determines approximately where a split-cast model or a model part is to be arranged. This concerns the height as well as the position in the surface plane of the base plate relative to the base plate. It is also possible to provide different adjustment aids for the height and for the position.

The adjustment aid can be installed e.g. on the base plate or on a plate surrounding said base plate; it can indicate the preferred height by means of a mark or it can indicate a possible height range by means of a plurality of marks. In the case of the model e.g. the gingival boundary or the preparation limit or the upper end of the model can be arranged relative to the height adjustment aid.

The adjustment aid for adjusting the position can comprise a transparent disk having provided thereon marks, such as lines or spots, which are indicative of specific reference points of the model. The disk can be arranged above the base plate, and the model can be observed through the disk with the marks for the purpose of adjustment.

The adjustment aid may also comprise a camera which is arranged at a defined position relative to the scanning area and which looks at the base plate. In a pictorial representation of the camera picture, information can be shown, such as lines or arrows, with which necessary corrections of the positioning of the model on the base plate are made visible. For example, a target position can be shown together with the actual position. The target position can also be indicated by schematic lines.

Another device for scanning a tooth model is provided with a holding device with the aid of which a split-cast model can be scanned.

For producing dental prosthesis elements, such as bridges or the like, it is normally necessary to record the relative arrangement of e.g. two neighbouring elements (e.g. two teeth), and to record simultaneously also the shape of each individual tooth. Due to shading effects, it is, however, difficult to effectively record the shape of a tooth in its entirety when the two teeth are juxtaposed. Recording of the juxtaposed teeth is, however, necessary so as to record the relative arrangement of the two juxtaposed teeth.

Hence, it will be of advantage when, on the one hand, scanning is executed when the various teeth occupy their positions relative to one another in a defined manner (survey scan) and when, on the other hand, scanning of each individual tooth is executed so as to record the shape of the respective tooth in its entirety (individual scan).

The present device is only provided with one holding device which can, however, be used for holding a plurality of teeth at their positions relative to one another and also for holding individual teeth, without any necessity of using two different holding devices.

When a tooth or teeth have been referred to hereinbefore or will be referred to hereinbelow, the statements made apply, of course, also to dental prosthesis elements, residual tooth areas, gingival areas or combinations thereof, e.g. a tooth with a dental prosthesis element which is arranged adjacent thereto. Dental prosthesis elements can e.g. be implants, implant abutments, bridges, inlays, overlays or the like.

According to an advantageous embodiment, the holding device comprises a deformable material, such as a plasticine or wax, for the purpose of holding. Pins of tooth models, of the type used in split-cast models, can easily be pressed into a plasticine, so as to obtain a tooth model. Furthermore, it will also be possible to place a larger model part onto a plasticine (even if said model part is not provided with pins), the adhesive effect of the deformable material being preferably sufficiently strong for holding this model. It will be advantageous to arrange the deformable material in a pot or on a plate. This plate or this pot can be arranged on the base plate, or they can be the base plate. In the first case, the base plate can have provided thereon a magnet for holding the holding device.

The above-described holding device can be of advantage independently of the device with a base plate. It may, however, also be used in combination with such a device. It will then e.g. be possible to arrange the holding device with the deformable material on the base plate.

According to another embodiment of a device for scanning tooth models, the device is provided with a loading unit. By means of said loading unit a plurality of tooth models and/or individual parts of a tooth model can be supplied to a holder successively or simultaneously.

This holder can e.g. be a holder consisting of a deformable material as has been described hereinbefore.

It will be advantageous when the loading unit comprises one or a plurality of cameras by means of which the position of the tooth models and/or of parts of a tooth model, e.g. part of a split-cast model, can be recorded. On the basis of the pictures recorded by the camera, it can be determined which locations are occupied by parts to be recorded.

According to an expedient embodiment, a robot arm is provided for inserting tooth models or parts of a tooth model into the holder. Making use of the cameras and the robot arm, the device for scanning tooth models can be loaded in a fully automatic manner. Other loading possibilities exist as well. For example, the tooth models can also be transferred by means of a conveyor belt to the device for the purpose of scanning. Also slide feed means or the like can be used for moving the tooth models.

In the case of a method for scanning a tooth model, the following steps are provided: the various model parts of a split-cast model are held by a model part holder and scanned in this configuration. In a further step, one or a plurality of model parts is scanned, each model part being adapted to be recorded independently of the other model parts. The two steps can be executed in an arbitrary sequence.

The use of a split-cast model with individual model parts and a model part holder has the advantage that the model parts held by the model part holder can be scanned in immediate succession and that the individual model parts can be scanned immediately afterwards. Hence, the one-piece tooth model need not be sawn into pieces between two scanning processes so that the scanning can be executed simply and easily.

According to an advantageous embodiment of the present method, the inner as well as the outer side of the split-cast model are scanned. A good overall survey of the tooth model is obtained in this way. The data acquired from the individual model parts can be combined, by means of data processing, with the data acquired from the model parts inserted in the model part holder (matching). For this purpose it will, in principle, suffice to scan the outer side or the inner side of a split-cast model. The use of data concerning the outer side as well as the inner side of the split-cast model will, however, provide an improved overall representation of the tooth model and also an improved matching result.

The scanning of the split-cast model in the first above-mentioned step can be executed by scanning a plurality of individual areas, each of said areas extending over a plurality of tooth sites. It is e.g. possible to scan a model, which represents a whole upper jaw or lower jaw, with 3, 4, 5 or 6 individual areas on the outer side and with a corresponding or a different number of individual areas on the inner side.

Between the scanning of the various individual areas, the model can be displaced and/or rotated so as to gain good access to the various areas to be scanned.

Each of the devices described can comprise a blackout means which will shade the objects to be scanned and protect them against the ambient light. This will improve optical scanning.

Each of the devices can be provided with an Internet connection. Internet updates will thus be possible. Also remote maintenance of the device will be facilitated or made possible in this way.

Furthermore, each of the devices can comprise an additional camera which is able to record images of various parts of the device and/or models. The camera can be used for remote maintenance. It also possible to use an already existing camera (e.g. from the adjustment or imaging system in the loading unit) for this purpose. The camera records preferably 2D images.

In the case of a device for scanning a tooth model a camera is provided for recording images. The images recorded can be images of device parts and/or of one or more models, such as split-cast models or parts thereof.

The camera is preferably part of an adjustment aid. The adjustment aid serves to facilitate the positioning of a tooth model to be scanned. For effective scanning, the tooth model must be arranged in a specific area relative to a respective scanning system. The adjustment aid is helpful for carrying out this positioning.

This positioning of the tooth model can be supported electronically by means of a camera which is part of an adjustment aid.

The camera itself is preferably arranged at a defined position relative to a scanning area and looks at a base plate of the device for scanning.

It is, however, also possible that the camera is not arranged at a defined position relative to the scanning area, but that marks are provided, which are arranged at a defined position relative to the scanning area and which can be recorded by the camera so that the position of the tooth model relative to such marks and, consequently, relative to the scanning area can be determined by evaluating the camera picture.

In accordance with a special embodiment, information is shown in a pictorial representation of the camera picture; by means of this information possibly necessary corrections of the positioning of the tooth model on a base plate are made visible. For this purpose, arrows or lines can be displayed in a pictorial representation. It is also possible to display coloured areas (e.g. green or red for correct or non-correct areas).

In addition, it is possible to show an actual position together with a target position, the target position being indicated e.g. by lines. These lines are preferably schematic, i.e. they do not concretely refer to a tooth model to be positioned, but they indicate quite generally, e.g. in outlines, a desired target position.

The adjustment aid can be arranged in a horizontal plane (x/y plane), i.e. in a surface plane of the base plate (x/y plane) for positioning the tooth model. Alternatively or additionally, it can, however, also be provided for adjusting the height (z direction) of a tooth model.

The camera preferably looks at a position of a tooth model which is arranged in the scanning area of the scanning system of the device. The whole tooth model can thus be perceived by the camera, and this will be advantageous for the purpose of adjustment.

According to a particularly advantageous embodiment, the camera is secured in position in or on a cover, the cover being used for covering the tooth model and/or the scanning system. The cover can be pivotable and it can also be part of a tunnel cover, the scanning system being slidingly moved into the tunnel or the tunnel being slidingly moved to a position covering the scanning system.

Such covers serve e.g. for shading the system and/or for protecting it against dust or the like.

The cover is preferably adapted to be moved into two defined positions, such as an open position and a closed position, the camera being directed to the position of a tooth model in the scanning area in at least one of the two positions or in both said positions.

This embodiment can be implemented e.g. such that, when the cover occupies the open position, the camera on/in the cover will look from above onto a tooth model in a scanning area so that the position can be adjusted in an x/y plane (horizontal plane or plane parallel to a base plate).

It is also possible that, when the cover occupies the closed position, the camera looks from above onto a tooth model in the scanning area.

At an open position, the camera can also be directed to a part outside of the device, e.g. for recording a picture of an operator for a conference call or of other models or parts outside of the system.

The camera can also be installed such that it is removable and that it can be re-installed at a defined position.

At the closed position, the camera can, as a result of the movement of the cover, e.g. also be arranged such that the height (z direction) can be adjusted.

Preferably, illumination means for illuminating a tooth model at a scanning position are provided. Such illumination means can comprise e.g. LEDs. These illumination means can be used for illuminating the tooth model and for perceiving it by a camera also in the closed condition of the cover or if the light conditions should be poor for some other reason.

The camera can additionally be used for remote maintenance.

Furthermore, the camera is implemented such that it records two-dimensional images (such as e.g. a normal (digital) still camera.

In addition, adjustment means can be provided with the aid of which an operator is able to vary the position of the tooth model for the purpose of adjustment. A tooth model can e.g. be held on a base plate by the magnetic force of a holding device, whereby the position of the tooth model can be varied by varying the position of the holding device. In addition, it is also possible to provide electrically controllable adjustment means (such as servomotors which are able to move a plate or a holding device) (or adjustment means that are controllable pneumatically or hydraulically or in some other way), which can be controlled by a computer. In this case, the positioning or adjustment of the tooth model relative to the scanning area can also be executed by a computer or at least with the aid of a computer.

Making use of a camera whose pictures can be evaluated electronically, it will then also be possible to execute an adjustment fully automatically, provided that the result of the picture evaluation is used for controlling the computer-controllable adjustment means.

The camera has preferably at least 10 000, 100 000 or 1 000 000 pixels. Such a number of pixels will suffice to execute the adjustment of the tooth model.

The tooth model is preferably a split-cast model.

Such a device comprising a camera can be combined with any feature of the devices described hereinbelow or above.

The applicant's German patent application DE 10 2005 016 233 "method and device concerning data transmission in dental prosthesis element production processes" of Apr. 8, 2005, is referred to in its entirety. The features which are specified in this application and which concern a scanning system for acquiring data sets can be provided, each individually or in an arbitrary combination, in the case of the device according to the present application. In particular the data remote transmission means including the camera for transmitting digital image data, and advantageous embodiments thereof, according to said German application (cf. e.g. claims 16 to 18 of said application) can be provided in the case of the device of the present application. Also the methods described in said German application (cf. e.g. claims 1 to 15) can be carried out by the device according to the present application, or suitable means can be provided for this purpose.

BRIEF DESCRIPTION OF THE DRAWINGS

Advantageous embodiments of the present device and of the present method are explained on the basis of the figures, in which.

DETAILED DESCRIPTION OF THE INVENTION

Figures 1A, 1B, 1C:
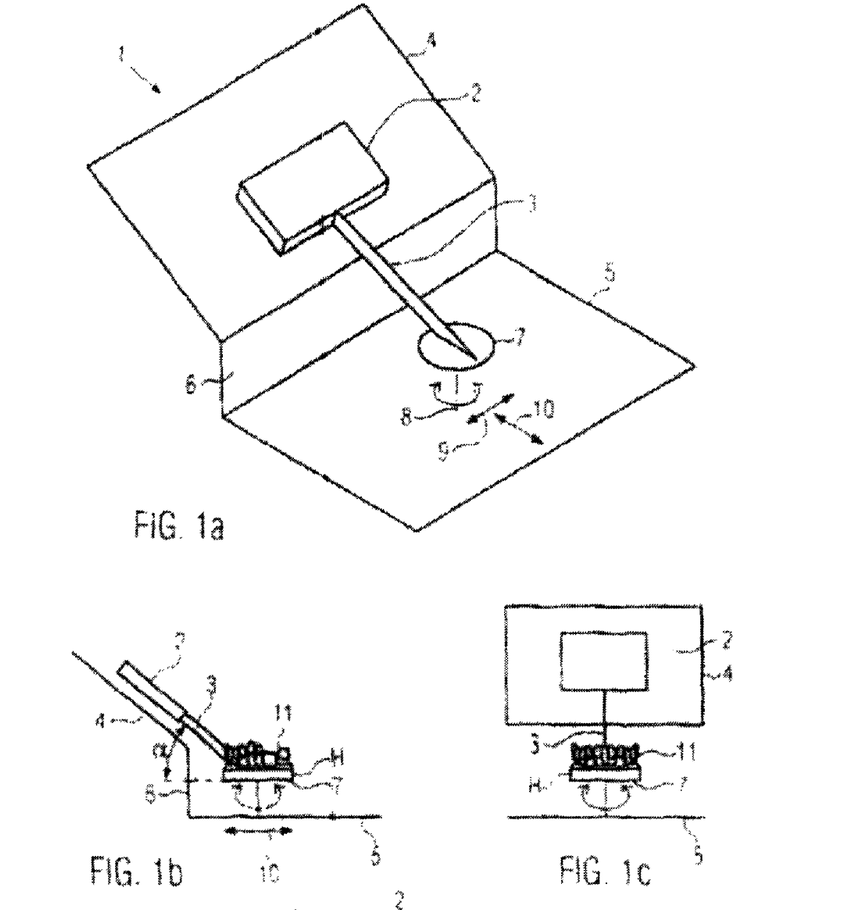
FIG. 1 shows schematic representations of a device for scanning tooth models.

FIG. 1a discloses a device 1 for scanning a tooth model in a three-dimensional schematic representation. The device is provided with a mounting plate 5 having arranged thereon a second mounting plate 4 which is held at an oblique angle via a carrier 6. The mounting plate 4 is arranged at an angle of 20° to 80°, or 35° to 60°, preferably approx. 45°, relative to the mounting plate 5. The mounting plate 4 supports an optical scanning system 2 which is capable of scanning models with a strip-shaped scanning area 3. Also the strip-shaped scanning area 3 is inclined at an angle of 20° to 80°, preferably 35° to 60°, even more preferably approx. 45° or larger or smaller than 45°, relative to the mounting plate 5 and the base plate 7, respectively.

The path of the laser light for illuminating the model with the laser line defines the strip-shaped scanning area 3 during laser line scanning.

In the case of laser line scanning, a plane is defined by the light of the laser line. In the case of phase shift scanning, a plane is defined by the centre of the illumination light. Normally, also the line of vision of the observation camera used for the phase shift method will lie in this plane. The line of vision encloses with the surface of the base plate preferably an angle of 20° to 80°. In this case, the line of vision will define the scanning area. The illumination and the camera can also be exchanged. In this case, the scanning area will be defined by the illumination. The central (optical) axis of the illumination will then extend at an angle of 20° to 80° relative to the surface of the base plate. The angles can also assume values between 35° and 60° or a value of approx. 45° or values above or below 45°.

The model can be arranged on a base plate 7. The base plate 7 is implemented as a rotary disk and provided with a rotary shaft 8; the rotary disk 7 can be rotated about the axis of rotation 8 in both directions or in only one direction.

The shaft 8 can be displaced in directions 9 and 10. The mounting plate 5 can be provided with suitable openings for this purpose so that it is a frame rather than a plate. Direction 9 lies in a direction transversely to the plane defined by the scanning area 3. Direction 10 lies in this plane and perpendicular to direction 9. By moving the shaft 8 in direction 9, a model can be displaced on the rotary disk 7 in a direction transversely to the strip 3. An area of the model can be scanned in this way. By displacing the shaft 8 in direction 10, the area scanned during displacement in direction 9 can be varied.

FIG. 1b shows a view of the device according to FIG. 1a parallel to the mounting plates 4 and 5. FIG. 1c shows a view of the device according to FIG. 1a along direction 10.

Figure 1D:
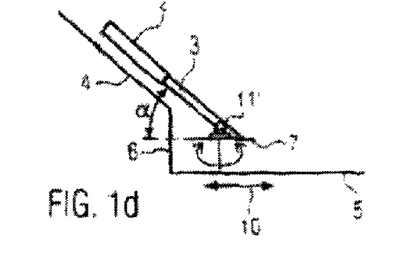

The surface of the base plate 7 and the scanning area 3 enclose between them an angle alpha (FIGS. 1b and 1d). This angle lies e.g. between 20° and 80°, 35° and 60°, or it is preferably an angle of approx. 45°. It allows a particularly good representation and scanning of the preparation limit, where a particularly good scanning of the model is desirable for well fitting dental prosthesis elements.

As can be seen in FIG. 1*b*, the relation between the centre of rotation of the model and that of the scanning area 3 can be varied by varying the height of the base plate 7 or of the model 11 above the base plate 7. In the case shown in FIG. 1*b*, an area of the model outside of the centre of rotation of the model is scanned. If the model were arranged further down, the scanning area 3 would scan an area that is located further inwards on the base plate 7 and closer to or next to the rotary shaft 8.

The base plate 7 has arranged thereon a holder H which holds a split-cast model 11. The holder H can e.g. be plasticine.

Whereas FIG. 1 shows an embodiment in the case of which the rotary disk 7 is fixedly connected to the rotary shaft 8, and the rotary shaft changes position due to displacement in directions 9 and 10 by means of e.g. x and y tables, other configurations are imaginable as well. For example, a rotating mechanism can releasably be connected to the rotary disk 7. For this purpose, a solenoid arranged below the rotary disk 7 on the shaft 8 can e.g. be switched on and off, or it can be moved away from the rotary disk or towards said rotary disk so as to increase the magnetic coupling. A permanent magnet can be provided for this purposes as well. It is also possible to provide a suction device which, by means of a vacuum, will fix the rotary disk at various positions for rotation.

For displacing the rotary shaft, the connection between the rotary shaft and the rotary disk is released, the rotary shaft is displaced (in direction 9 or 10), and the connection is then reestablished at some other point. The connection can be established by a solenoid, a permanent magnet or a suction device or the like. When not held by the rotary shaft 8, the rotary disk 7 can rest on a support which has an opening that can be used for passing the rotary shaft 8 therethrough, but which supports the outer circumference of the rotary disk 7. On the basis of this configuration, rotations of the rotary disk 7 about axes other than the centre of the rotary disk 7 are possible.

Figure 2A:
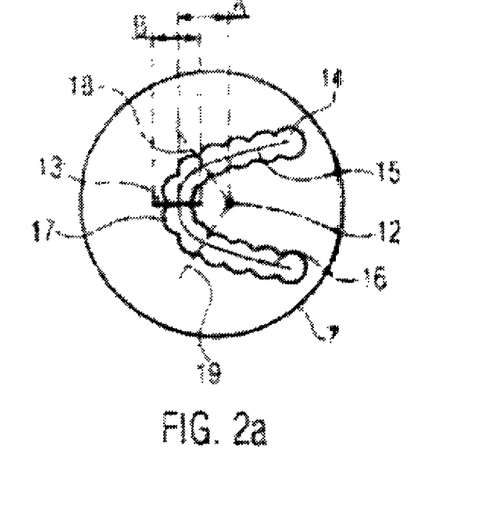
FIG. 2 shows schematic representations of the top view of a base plate and of side views with a split-cast model and a model part.

FIG. 2*a* shows a tooth model 14 on a rotary disk 7. The tooth model 14 comprises two essentially linear pieces 15, 16 connected to an arcuate piece 17 (dental arch). The centre of the arcuate piece 17 is designated by reference numeral 12. Virtually any set of teeth of a human being has such a configuration. The transitions between the linear pieces 15, 16 and the arcuate piece 17 are indicated by the broken lines 18 and 19.

For scanning the arcuate piece 17, it will be advantageous to rotate the rotary disk 7 about the centre 12. The area that can be covered by the strip-shaped scanning area 3 is identified by the line designated by reference numeral 13'. It has a width B which is measured in the plane of the base plate 7 and which is between 5 mm and 80 mm. By rotating the rotary disk 7, the area of the tooth model 14 lying between the broken lines 18 and 19 can be scanned in. Attention should here be paid to the fact that the centre 12 lies outside of the area 13' that can be covered by the scanning area. The rotary shaft of the rotary disk 7 is here positioned at the least possible distance from or on the centre 12 of the arcuate piece 17. The distance between 12 and the centre of the scanned area B is designated by A.

Scanning can be executed during the rotation of the rotary disk 7 or it can also be executed by a (preferably linear) displacement in a direction transversely to the scanning area (in FIG. 2*a* upwards or downwards). In the latter case, the piece 17 can be scanned by scanning individual areas; due to the fact that neighbouring areas overlap, the data of the individual areas can be combined by a matching process. Between the scanning of these individual areas, the rotary disk is rotated a bit further about its rotary shaft so as to scan the next individual area and so as to scan, step by step, the entire piece 17. These composite data represent the data of the survey scan.

Figure 2B:
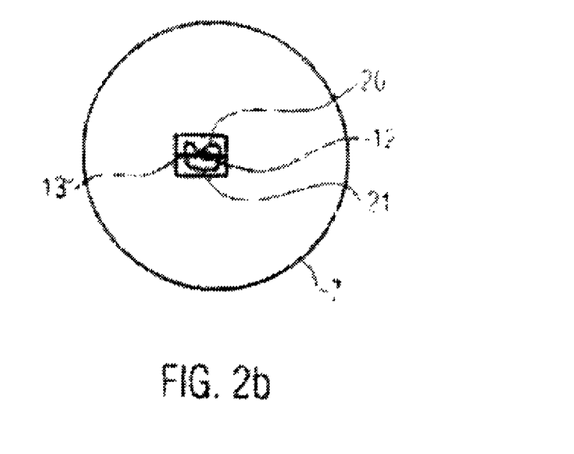

In the case shown in FIG. 2*b*, a model 20 of an individual tooth 21 is arranged on the rotary disk 7. The tip of the tooth is designated by reference numeral 12. For allowing effective scanning of the model of said tooth 21 from all sides, it should be possible to rotate the tooth relative to the scanning area. A rotation about point 12 will here be of advantage. It would, however, be expedient to position the scanning area 13" such that it is located near the desired axis of rotation 12.

By displacing the rotary shaft of the rotary disk relative to the scanning area, it is possible to obtain a configuration (between rotary shaft and scanning area) of the type shown in FIG. 2*a* as well as a configuration of the type shown in FIG. 2*b*. This is also possible by adjusting the height of the base plate and/or of a holding device.

Figure 2C:
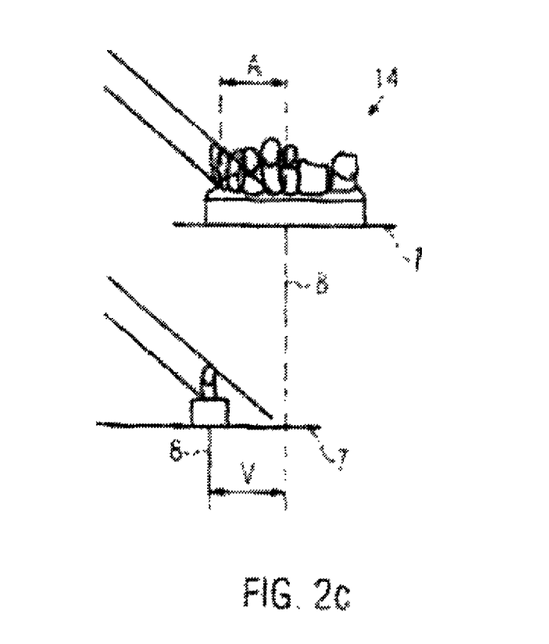

FIG. 2*c* shows, in the upper half of the figure, a case where a survey scan of the split-cast model is to be made. The rotary shaft 8 is positioned approximately at the centre 12 of the dental arch 17. The scanning area lies at the dental arch. In the lower half of FIG. 2*c*, a model element of an individual tooth is arranged at the rotary shaft 8. Hence, it can be rotated without leaving the scanning area. In order to allow this, the rotary shaft 8 must be displaced by an amount V in comparison with the upper half of FIG. 2*c*. V amounts e.g. to 22.5 mm.

Figure 2D:
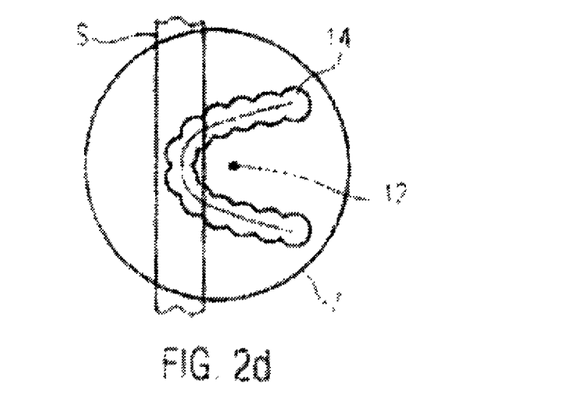
Figure 2E:
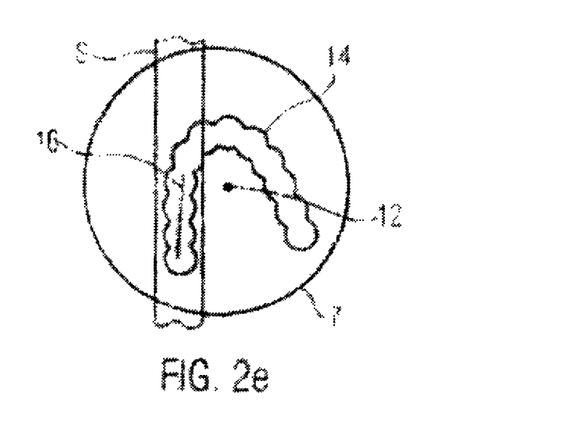

By displacing the base plate 7 below the scanning area 13 in a direction transversely to the scanning area 13, a strip-shaped area can be scanned on the base plate. This strip-shaped area is designated by the reference symbol S in FIG. 2*d*. As can be seen, the dental arch can be scanned quite well. By means of a rotation about the dental arch centre 12, the linear piece 16 (or at least the outer side thereof) can be moved fully into the strip S where it can be scanned preferably in one go.

Figure 2F:
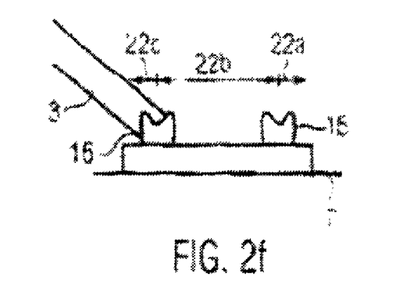
Figure 2G:
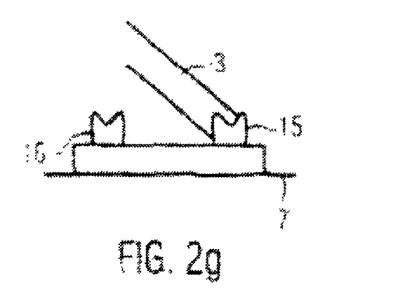

If it should be desired to scan both the outer and the inner area of the model 14, a displacement of the rotary disk will be advantageous once more. FIG. 2*f* and FIG. 2*g* show sectional views of the rotary disk 7. The model 14 has been rotated clockwise by approx. 90° in comparison with FIG. 2*a*. The outer area of the tooth model is designated by reference numeral 22*a* and the inner area by reference numeral 22*b*. It will be expedient to scan the outer area 22*a* from outside and the inner area from inside so as to avoid shading. In order to achieve this, the rotary disk 7 or rather the rotary shaft thereof is displaceable. As can be seen in FIG. 2*f*, this allows the outer area 22*a* of piece 16 to be scanned from outside and the inner area 22*b* of piece 15 to be scanned from inside (cf. FIG. 2*g*). In FIG. 2*g*, the rotary disk 7 with the model has been displaced in comparison with FIG. 2*f*. The displacement is here larger than in the case of FIG. 2*c*. The necessary displacement can be as large as 100 mm.

The displacement can also be so large that the base plate is displaced up to and into a loading position where the model can easily be installed and removed.

The various displacement means can be given in respective pairs or all three together by one and the same displacement means. Each of the displacement means can, however, also be independent of the other ones. They may, however, also overlap one another (example: two linear tables are mounted such that one will be able to move the other and that the respective directions of movement are equal (or different).

Figure 3A:
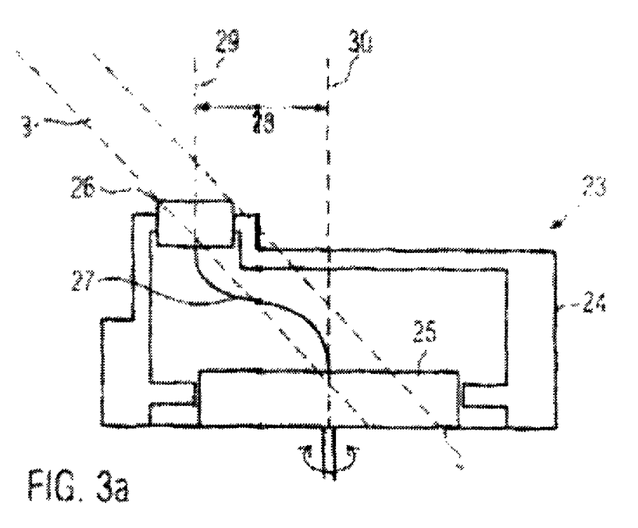
FIG. 3 shows various schematic sectional views of adapters.
Figure 3B:
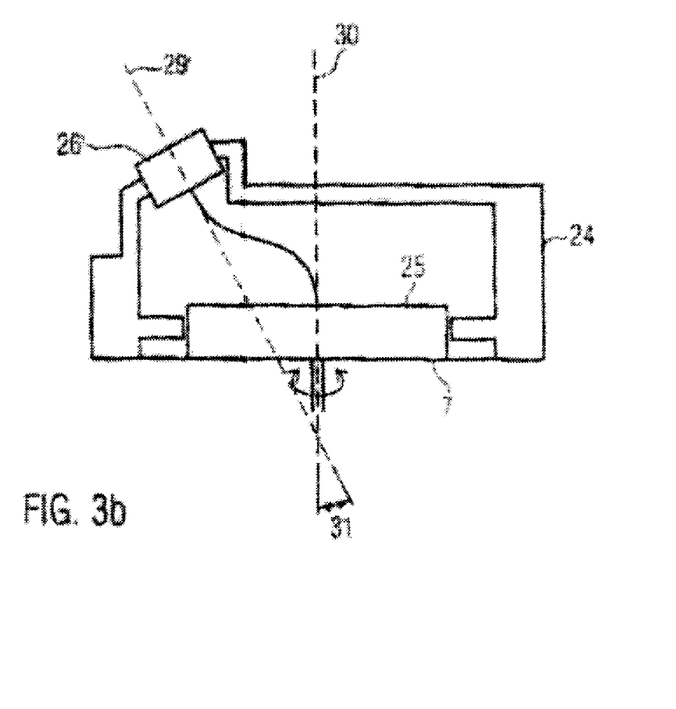

FIGS. 3a and 3b show adapters 23 by means of which the axis of rotation can be displaced relative to the scanning area. FIG. 3a shows the rotary disk 7 with the axis of rotation 30. For scanning a small model piece, e.g. the model of an individual tooth, a rotary element 26 is provided. This rotary element can be rotatably supported in a housing 24. The adapter additionally comprises an element 25 which can be connected to the rotary disk 7 by a non-positive connection. This can be accomplished by a suitable shape of the rotary disk and of the element 25, e.g. through pins and holes or grooves and projections or the like, and also e.g. by a magnetic force acting between the element 25 and the rotary disk 7.

The rotary element 26 and the element 25 are interconnected by a (flexible) shaft 27 which transmits the rotation of the element 25 to the rotary element 26. Instead of a shaft 27, it is also possible to use gears in a suitable gearing arrangement, toothed belts or the like for transmitting the rotation. The element 25 itself is rotated by the rotation of the rotary disk 7. The rotary element can have arranged thereon a tooth model. For this purpose, a deformable material (e.g. plasticine) can be provided on or in the rotary element or in a pot secured to said rotary element.

The housing 24 of the adapter 23 is supported in a stationary manner outside of the rotary disk 7.

As can be seen from FIG. 3a, the axis of the relevant rotation is displaced from the axis of rotation 30 of the rotary disk 7 by the distance 28 towards the axis of rotation 29 of the rotary element 26. The displacement takes place in the plane defined by the scanning area 3.

In comparison with FIG. 3a, the rotary element 26' has been tilted in FIG. 3b. The axis of rotation 29' of the rotary element 26' therefore extends at an angle 31 relative to the axis of rotation 30. This angle is preferably an angle between 5° and 40°, e.g. 15° to 25°, preferably approx. 20°. The angle 31 should preferably be an angle between the angle enclosed by the scanning area 3 and a perpendicular on the mounting plate 5 or a perpendicular on the rotary disk 7.

Figure 4A:
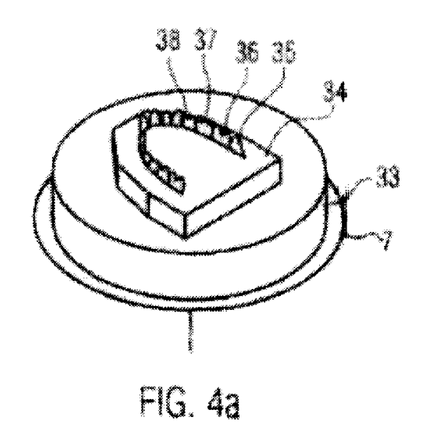
FIG. 4 shows various schematic representations of a holder.
Figure 4B:
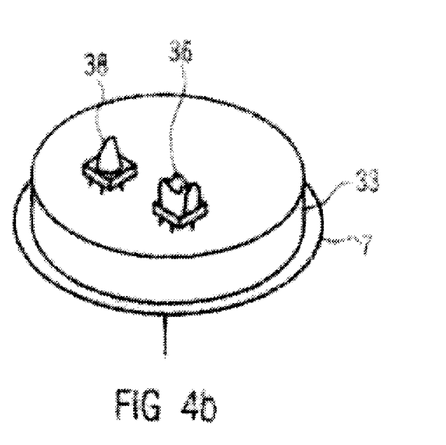

FIG. 4a shows a rotary disk 7 having a holding device 33 arranged thereon. The holding device 33 comprises a deformable material, e.g. plasticine. A tooth model can be arranged on this plasticine by placing it on top of said material, where it will be held by the plasticine. Due to the static friction between the tooth model and the deformable material 33, the model will be sufficiently held.

The deformable material is here placed on the rotary disk in a cylindrical shape. The rotary disk may, however, also be provided with a pot in which the deformable material is arranged.

The model is here, in an exemplary embodiment, a split-cast model. In this case, a model part holder 34 is provided, which has inserted therein, with the aid of pins or other means, individual model parts corresponding to one or more tooth sites. The various model parts are here exemplarily designated by reference numerals 35 to 38. These model parts 35 to 38 can be removed individually from the model part holder 34. They can be pressed with the pins into the deformable material 33. Hence, they will be held, loosely but still to a sufficient extent, for being subjected to the scanning process. This scanning will preferably be optical scanning, since during such optical scanning no forces will be applied to the model parts.

By means of the deformable material 33, it is therefore possible to hold an entire split-cast model as well as individual parts of such a split-cast model so that only a single holder will be required, without any necessity of using two different holders.

A mask made of paper or metal can be arranged, permanently or temporarily, on the deformable material, said mask predetermining the approximate positions of the individual parts.

Figure 5A:
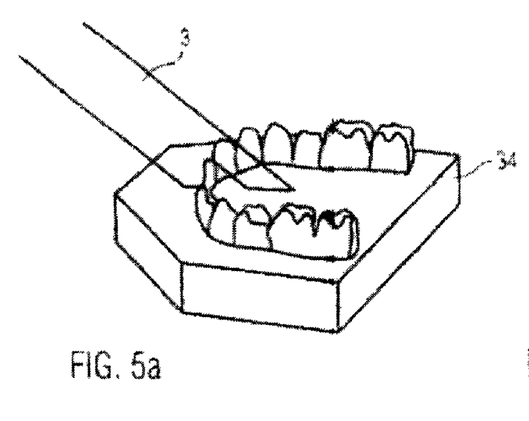
FIG. 5 shows various method states during execution of the method.

FIG. 5a shows a split-cast model located in the scanning area 3. By rotating/displacing the split-cast model, the positions which the various model parts occupy relative to one another in the model can be recorded. The model shown is a split-cast model with a model part holder 34.

The configuration shown in FIG. 5a can only be used for scanning the outer side of the teeth. For scanning the inner side as well, the split-cast model must be displaced in a suitable manner.

It will, in particular, be advantageous to scan the outer sides as well as the inner sides of the tooth models.

Figure 5B:
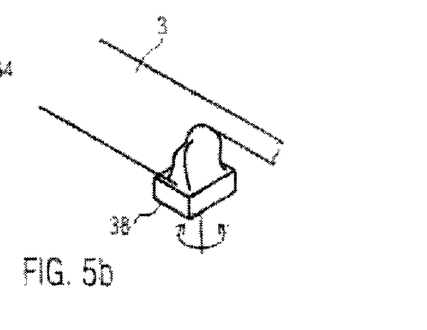

When the tooth model in its entirety has been optically scanned, the model parts of the split-cast model will be removed from the model part holder 34. Subsequently, each individual model part will be scanned, as can be seen in FIG. 5b. For this purpose, the tooth model 38 can either be scanned while it is being rotated, so as to scan the tooth model on each side thereof, or the tooth model can be linearly displaced through the strip-shaped scanning area 3 and rotated between the individual displacement processes. Also this will allow, on the basis of digital matching of the data acquired, to obtain a complete digital image of the tooth model 38.

The data acquired in the course of the step shown in FIG. 5b can then be digitally processed with the data acquired in the course of the step shown in FIG. 5a, so as to digitally obtain by means of a matching process an image of the tooth model which is as accurate as possible in every detail.

Figure 6:
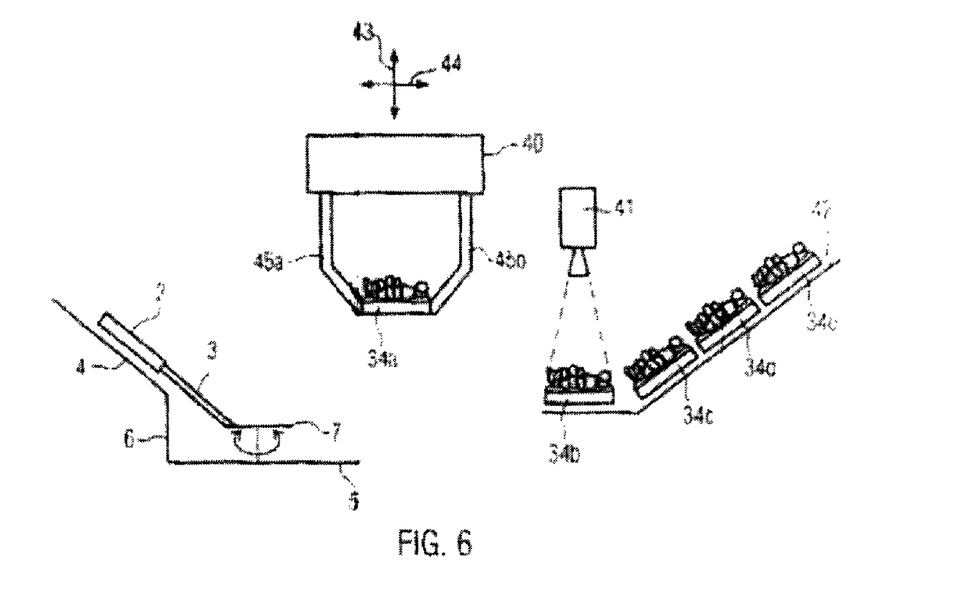
FIG. 6 shows a schematic representation of a loading unit.

FIG. 6 shows a device for scanning tooth models, which is provided with a loading unit. The loading unit comprises a camera 41 with which tooth models 34a to 34e can be recorded individually or in combination. The tooth models are stored on a conveyor path 42, which can be implemented as a chute, as a conveyor belt or the like. The individual tooth models 34a to 34e can be inserted in the tooth model scanning device by means of a robot arm 40. The robot arm 40 can be moved up and down in direction 43 and to the right and to the left in direction 44. A movement transversely to the plane of the drawing is possible as well so as to have the maximum flexibility.

The robot arm can take hold of a tooth model 34a with gripper arms 45a and 45b. It is thus possible to insert the tooth model 34a in the device for the purpose of scanning or to remove it from said device. The robot arm is preferably implemented such that it will also be able to remove individual model parts of a split-cast model from a model part holder. Hence, it will also be possible to automatically load individual model parts for subjecting them to a scanning process.

It will be expedient to implement the device such that, by means of the robot arm or some other mechanical, automatic operating element, all the models or model parts can be loaded, without any human activity being necessary, for subjecting them to the various scanning processes.

Figure 7A:
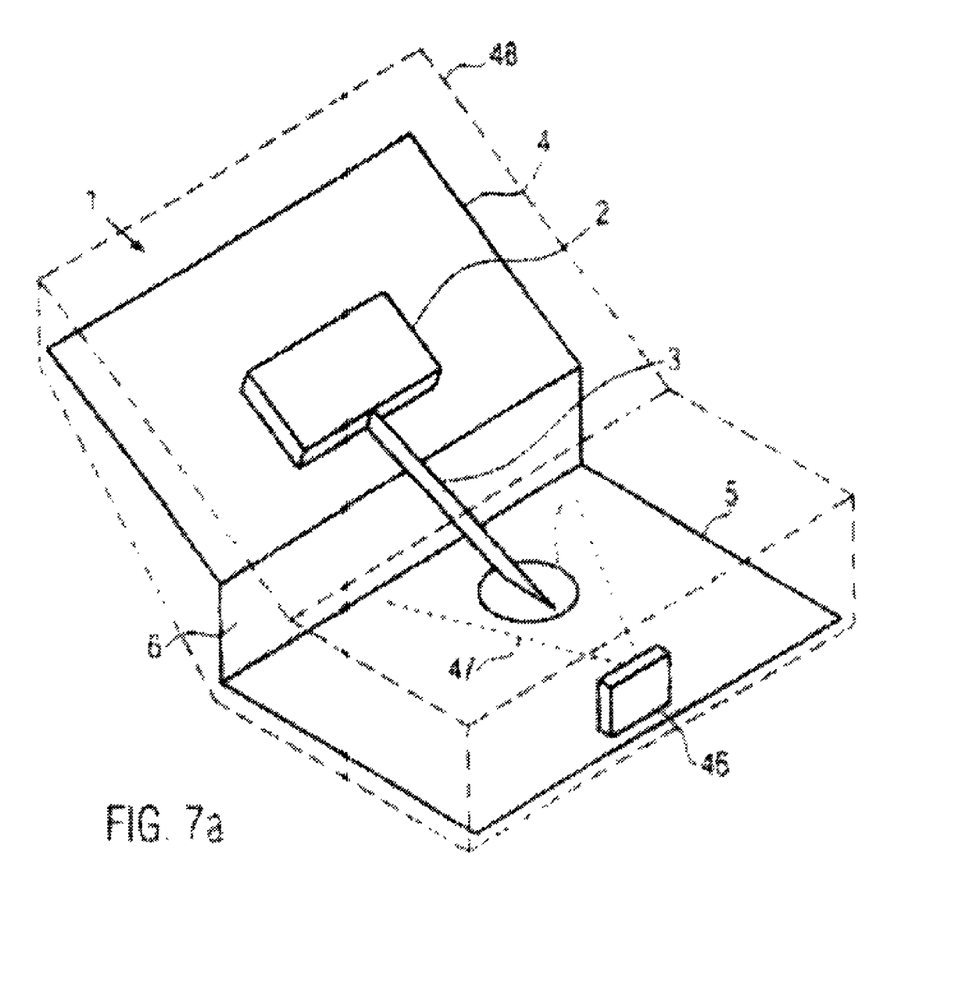
FIG. 7 shows a schematic view of a device for scanning with a cover.

FIG. 7a shows schematically a device 1 for scanning tooth models. The scanning device 1 is provided with a cover 48 which is able to cover the optical scanning system 2. The cover 48 serves to reduce or exclude ambient light as well as to protect the optical components against dust or the like.

In FIG. 7a the camera 46 is secured to the cover 48 and looks at the scanning area of the scanning system 2. The field of vision is larger than the scanning area so that the camera will be able to record also a tooth model which is not positioned in the scanning area. With the aid of the camera 46, a user will be able to position the tooth model correctly in the scanning area and he will also be able to position it in the correct orientation. The representation in FIG. 7*a* allows in particular an adjustment of the z position (height above the mounting plate 5).

Figure 7B:
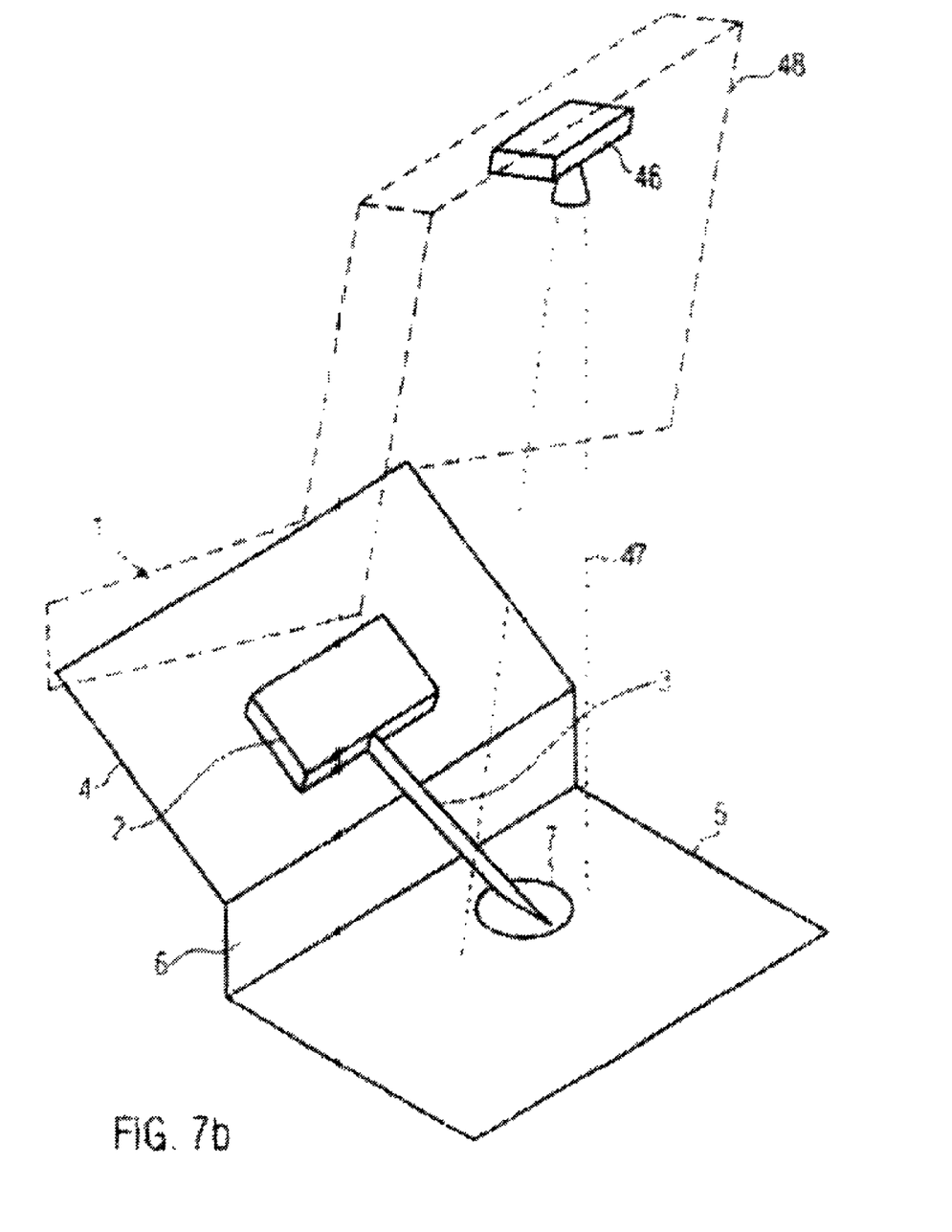

FIG. 7*b* shows the device according to FIG. 7*a* in the open condition of the cover 48. The cover is held at this position e.g. by supports, pneumatic springs (neither of them shown) or the like. The camera 46 now looks from above onto the scanning area of the scanning system 2. The line of vision 47 of the camera 46 need not be precisely perpendicularly from above, as shown in FIG. 7*b*, it may also be a line of vision at an oblique angle. When the cover occupies the position according to FIG. 7*b*, especially the x-y position can be adjusted.

The fact that the camera 46 is secured to the cover 48 makes additional camera holding components superfluous.

The invention claimed is:

1. A method of scanning a split-cast model, comprising the following steps, which can be executed in an arbitrary sequence:
holding the various model parts of a split-cast model by a model part holder and scanning the various model parts while being held by the model part holder; and
making one or a plurality of additional individual scans, wherein during an individual scan an individual model part of the various model parts of the split-cast model is scanned; and prior to scanning
removing the individual model part from the model part holder and holding the individual model part independently of the model part holder; or
retaining the individual model part in the model part holder while removing adjoining model parts so as to improve the optical accessibility of the individual model part.

2. A method according to claim 1, characterized in that the inner as well as the outer side of the split-cast model are scanned.

3. A method according to claim 1, characterized in that the data acquired from the individual model parts are combined, by means of data processing, with the data acquired from the model parts inserted in the model part holder.

4. A method according to claim 1, characterized in that, in the first step, scanning of the split-cast model is executed by scanning a plurality of individual areas, each of said areas extending over a plurality of tooth sites.

5. A method according to claim 4, characterized in that a model, which represents a whole upper jaw or lower jaw, is scanned with 3, 4, 5 or 6 individual areas on the outer side and with a corresponding or a different number of individual areas on the inner side.

6. A method according to claim 4, characterized in that the model is displaced and/or rotated between the scanning of the various individual areas.

* * * * *